United States Patent [19]

Ebert et al.

[11] Patent Number: 5,413,919
[45] Date of Patent: May 9, 1995

[54] METHOD FOR PREPARING FROM CULTURED CELLS A THROMBOPLASTIC REAGENT SUITABLE FOR USE IN THE PROTHROMBIN TIME TEST

[75] Inventors: Ray F. Ebert, Derwood; Rafael P. Valdes-Camin, Germantown, both of Md.

[73] Assignee: Akzo N.V., Arnhem, Netherlands

[21] Appl. No.: 263,410

[22] Filed: Jun. 21, 1994

Related U.S. Application Data

[63] Continuation of Ser. No. 904,423, Jun. 26, 1992, abandoned, which is a continuation-in-part of Ser. No. 781,511, Oct. 22, 1991, abandoned.

[51] Int. Cl.$^6$ .......................... C12P 21/02; C12P 1/00; C12Q 1/56
[52] U.S. Cl. .................. 435/70.3; 435/70.1; 435/41; 435/13
[58] Field of Search ............... 435/70.1, 70.3, 70.4, 435/13, 41

[56] References Cited

U.S. PATENT DOCUMENTS

| | | | |
|---|---|---|---|
| 3,980,432 | 9/1976 | Trobisch et al. | 23/230 B |
| 4,416,812 | 11/1983 | Becker et al. | 435/13 |
| 5,147,803 | 9/1992 | Enomoto | 436/176 |
| 5,254,350 | 10/1993 | Barrow et al. | 435/13 |

OTHER PUBLICATIONS

Abstract of Hungarian T048,906 (12/87).
Abstract of French 1,348,541 1/64.
Abstract of French 2409M 4/64.
Abstract of U.S. 4,784,940 (6/87).
Abstract of EP 162,977 (5/84).
Abstract of DT 2,915,310 (4/79).
Abstract of EP 107,383 (9/82).
Abstract of WO 9,005,740 (11/88).
Abstract of DE 3,150,596 (12/81).
Abstract of FR 1,348,542 1/64.
Abstract of EP 347,262 (6/88).
Abstract of WO 9,005,530 (11/88).
Abstract of WO 8,809,817 (6/87).
Abstract of EP 278,776 (2/87).
Abstract of WO 8,807,543 (3/87).
Leoni, P. et al., Thromb. Res. 46:737–738 (1987).
Computer Abstract of Vijaya, L. et al., Thromb. Res. 51:4:373–384 (1988).
Computer Abstract of Conklin, P. R. et al., Blood 72:1:128–133 (1988).
Computer Abstract of Carson, S. D., et al., Thromb. Res. 41:2:185–195 (1986).
Computer Abstract of Van Wijngaarden, et al., Thromb. Res. 43:3:265–274 (1986).
Computer Abstract of Naito, S., et al., Gann. 74:2:240–247 (1983).
Computer Abstract of Rothberger, H. et al., J. Clin. Invest. 62:3:649–65 (1978).
Computer Abstract of Maynard, J. R., et al., Blood 50:3:387–396 (1977).
Computer Abstract of Schone, A. et al., Arch. Dermatol. Res. 281:5:316–320 (1989).
Computer Abstract of Smariga, P. E., et al., Biochim. Biophys. Acta 76:1:109–118 (1983).

(List continued on next page.)

Primary Examiner—Douglas W. Robinson
Assistant Examiner—Kristin Larson
Attorney, Agent, or Firm—Jeffrey L. Ihnen; William M. Blackstone

[57] ABSTRACT

A method for preparing a thromboplastin reagent from cultured human cells comprising the steps of washing the cells with isotonic aqueous salt solution, lysing the cells by hypotonic shock, and resuspending the cell lysate in a diluent compatible with a one-stage prothrombin time determination to reach a concentration of about 0.5 to 3.0 mg/mL thromboplastin, whereby the cell lysate thromboplastin suspension produces a clot in a one stage prothrombin time test in about 10 to 15 seconds, with a mean normal prothrombin time of about 11–13 seconds, when added to citrated normal plasma in a volume ratio of about 2:1, such thromboplastin reagent being stable for at least 8 hours at 37° C. and for at least 5 days at 4° C.

9 Claims, 4 Drawing Sheets

OTHER PUBLICATIONS

Computer Abstract of Maynard, J. R., et al., *J. Clin. Invest.* 55:4:814–824 (1975).
Sakuragawa, N. et al., *Thromb. Res.* 10:457–458 (1977).
Chemical Abstracts—CA83:129418k—Liu, D. et al., *Thromb. Res.* 7:1:199–211 (1975).
Chemical Abstracts—CA99:32607p—Boddey, Y., *Aust. J. Med. Lab. Sci.* 4:1:5–27 (1983).
General Diagnostics, Simplastin package insert, Feb. 1984.
Behring, Thromborel S package insert.
Leoni, P., et al.; Thrombosis Research, 40, pp. 199–205, 1985.
Hetland, O., et al; Biochem J., 228, p. 735–743, 1985.
Bach, R., et al; The Journal of Biological Chemistry, 256(16), pp. 8324–8331, 1981.
Siama Catalog. 1991, p. 1513–1514, 2066.
Andoh, K. et al., "Amer. J. Clin. Pathol." 93:679–684 (1990).
Biggs, R., *Human blood Coagulation, haemostasis and Thrombosis*, 2nd Edition Blackwell Scientific Publications, London. (1976).
Drake, T. A. et al, "Am. J. of Pathol.," 134:1087–1097 (1989).
Hirsch, J. et al., "Chest," 95:5S–11S, (1989).
Hvatum, M. et al., "biochim. Biophys. Acta," 130:92–101 (1966).
Kirkwood, T. B. L., "Thromb. Hemostas.," 49:238–244 (1983).
Levy, G. A. et al., "J. Exp. Med.," 151:1232–1244 (1980).
Naito, S. et al., "Gann," 74:240–247 (1983).
Nemerson, Y., "Blood," 71:1–8 (1988).
Nemerson, Y. et al., "Hemostas. Thromb.," 6:237–261 (1982).
Quick, A. J. et al., "Am. J. Med. Sci.," 190:501–511 (1935).
Quick, A. J. et al., "J. Am. Med. Assoc.," 110:1658–1662 (1938).
Rappaport, S. I., "Ann. NY Acad. Sci.," 614:63–75 (1991).
Rehemtulla, A. et al., "Thromb. Hamostas.," 65:521–527 (1991).
Siverberg, J. M. et al., "Cancer Res.," 49:5443–5447 (1989).
Spicer, E. K., et al., "Proc. Natl. Acad. Sci. USA," 84:5148–5152 (1987).
Tsao, B. P. et al., "J. Exp. Med.," 159:1042–1057 (1984).
van den Besselaar, A. M. H. P. et al., "Thromb. Haemostas.," 65:263–267 (1991).

METHOD FOR PREPARING FROM CULTURED CELLS A THROMBOPLASTIC REAGENT SUITABLE FOR USE IN THE PROTHROMBIN TIME TEST

This application is a continuation of application Ser. No. 07/904,423, filed Jun. 26, 1992, now abandoned, which is a continuation-in-part of application Ser. No. 07/781,511, filed Oct. 22, 1991, now abandoned.

BACKGROUND OF THE INVENTION

This invention relates to the field of clinical hematology and specifically to coagulation factor monitoring of human plasma.

The prothrombin time test

The prothrombin time (PT) test is one of several clinical hematology assays of plasma in which the result is based on the time required to form a fibrin clot. It provides diagnostically useful information regarding the patency or functional integrity of coagulation factors involved in the tissue factor pathway (formerly known as the extrinsic coagulation pathway; Rapaport, 1991), viz. factors I, II, III, V, VII, and X. It also is useful for monitoring patients receiving oral anticoagulant therapy. In practice, this test is most sensitive to the concentration and/or activity of coagulation factors V, VII, and X.

Plasma deficient or defective in one or more of the above-mentioned coagulation factors typically yields a PT that is >20% longer than the average PT obtained from a group of normal plasma samples. Thus, the prothrombin time represents a useful means of detecting clotting factor deficiencies and monitoring the level of oral anticoagulation.

Thromboplastins

The PT test requires a "thromboplastin" to initiate the clotting reaction. A thromboplastin may be defined generally as a substance having clot-inducing properties or activity. In the specific context of a PT test, the thromboplastin contains substantial amounts of tissue factor (coagulation factor III), an essential cofactor for the activation of coagulation factor VII (Nemerson, 1988). Generation of activated factor VII initiates a cascade of additional reactions culminating in the formation of a fibrin clot. Such a clot can be detected manually by visual inspection or automatically by means of instrumentation designed to monitor solution viscosity or translucency.

In the past, many laboratories manufactured their own thromboplastins from human or animal tissues. This practice led to highly variable reagents that yielded mean normal plasma clotting times from approximately 11–20 sec. Since these locally produced thromboplastins did not contain calcium, the one-stage PT test actually was a two-step procedure performed by (1) mixing 0.1 mL of citrated normal plasma with 0.1 mL of thromboplastin, and (2)—after warming the mixture to 37° C.—initiating the clotting reaction by addition of 0.1 mL of 0.025M $CaCl_2$ (Biggs, 1976; p. 330; p. 677).

During the past 20 years commercially available thromboplastins have come into widespread use. As a consequence, the vast majority of clinical hematology laboratories have ceased making their own thromboplastins, and several modifications have been made to the classical procedure for a PT test, notably: (1) Since all commercial thromboplastins now contain calcium, the original "two-step" procedure has been supplanted by a "one-step" or true one-stage assay whereby 0.1 mL of citrated normal plasma is combined with 0.2 mL of calcium-enriched thromboplastin; and (2) since commercial thromboplastins generally are less variable and more active than classical thromboplastins, acceptable ranges for the clotting time of normal plasma have been reduced to about 10–14 sec, with mean normal prothrombin times of about 11–13 sec.

To emphasize the distinction between a thromboplastin formulated via classical methods and used in the two-step procedure versus current commercially available thromboplastins that contain calcium and are used in the one-step procedure, we shall refer to the latter as a "thromboplastin reagent."

It is this present-day definition of a one-step/one-stage PT test, and this present-day formulation of a calcium-enriched thromboplastin reagent that defines and relates specifically to the subject of this invention: A thromboplastin reagent suitable for use in the PT test.

Current specifications for the prothrombin time test

It is important and highly pertinent to the premise of the present invention that a new and useful thromboplastin reagent suitable for the PT test must meet or exceed the performance characteristics of commercially available thromboplastin reagents currently employed by clinical laboratories for this purpose. That is, (i) as described above, it should be a one-step/one-stage clot-based assay (ii) clotting times for normal plasma should range from approx. 10–14 sec, with a mean normal PT of about 11–13 sec; (iii) when compared with an international reference thromboplastin reagent against a panel of normal and coumadin-anticoagulated plasma samples, using generally accepted methodology (vide infra), a scattergram of the logarithms of clotting times should exhibit a high positive correlation; and (iv) a useful thromboplastin reagent will be stable under conditions of normal use. The foregoing characteristics and additional information regarding procedures and performance of thromboplastin reagents suitable for use in the PT test are further described in package inserts for the commercial SIMPLASTIN ® thromboplastin reagent (Organon Teknika Corp., Durham, N.C.); Dade Thromboplastin C thromboplastin reagent (Baxter Healthcare Corp., Dade Division, Miami, Fla.); Ortho rabbit brain tissue thromboplastin (Ortho Diagnostics Systems, Raritan, N.J.); and THROMBOREL ® S thromboplastin reagent (Behrinkerke AG, Marburg, Germany), which are incorporated herein by reference.

Methods for preparing thromboplastins

The classical method of preparing a thromboplastin for the PT test was first described by Quick et al. (1935; 1938). The Quick thromboplastin (Quick, 1938) was prepared from minced rabbit brains by a process involving the steps of (1) dehydration and partial delipidation of the minced tissue by repeated washing with acetone, followed by drying at 37° C.; (2) reconstitution of the acetone powder (0.3 g) in "5 cc. of physiologic solution of sodium chloride containing 0.1 cc of sodium oxalate" (i.e., a 5 mL aqueous solution containing approx. 0.15M NaCl plus 0.002M $Na_2C_2O_4$); (3) incubation of the suspension at 45° C. for 10 min; and (4) low-speed centrifugation for 3 min to remove large particles. Thromboplastin activity remains in the "milky supernatant liquid."

The original method of Quick et al., with minor modifications (Biggs, 1976; pp. 663–664), has served as the basis for present-day thromboplastin reagent preparation methods. Alternative methods are also known: For example, Biggs (1976; p. 664) teaches a method involving maceration of whole brain "for about 2 minutes with warm 0.85 per cent saline in a Waring blender." This method is but a slight modification of the Quick method, notable for its omission of the acetone extraction/dehydration step. In a second example, Hvatum& Prydz (1966) teach a method involving detergent extraction of a microsomal fraction from human brain, followed by dialysis against buffered saline solution to remove the detergent, which inhibits tissue factor activity. Because of the need to prepare microsomes by high-speed centrifugation and to remove detergent by dialysis, this method is cumbersome and not amenable to the preparation of large quantities of thromboplastin required for commercial applications.

Summarizing, the current state of the art for production of a thromboplastin reagent (from human or animal tissues) suitable for use in the PT test involves (1) selection of an appropriate tissue with high thromboplastin (tissue factor) activity [e.g., rabbit, bovine, or human brain; human placenta; or rabbit or bovine lung]; (2) dehydration and partial delipidation of the minced tissue with acetone, with further drying at ambient or elevated temperature to yield an acetone powder, and reconstitution of the acetone powder in an appropriate diluent, or tissue maceration; and (3) removal of large particles by centrifugation. Thromboplastin reagent also may be formulated via modifications to steps 2 and 3 as described above.

Methods for evaluating thromboplastin reagents

Commercially available thromboplastin reagents are of two general varieties: heterologous thromboplastins such as those derived from animal tissues (e.g., rabbit brain or bovine lung), and homologous thromboplastins such as those derived from human tissues (e.g., human placenta). As reviewed by Kirkwood (*Thromb. Haemostas.* 49:238-244, 1983) and Hirsh et al. *Chest* 95:5S-11S, 1989) thromboplastin reagents vary in their ability to detect the reductions in clotting factor activity induced by oral anticoagulants. It is generally recognized that homologous thromboplastin reagents are more sensitive to these changes in clotting factor activity than their heterologous counterparts. This increased sensitivity is desirable because it (i) permits better control of anticoagulant therapy and thereby reduces the risk of abnormal bleeding due to over-anticoagulation and (ii) increases the reagent sensitivity to minor abnormalities in coagulation factors of the tissue factor pathway.

One measure of the quality or sensitivity of a thromboplastin reagent is the "International Sensitivity Index" (ISI), which is calculated from an orthogonal regression of a test thromboplastin reagent against a reference thromboplastin reagent (as reviewed by Kirkwood and Hirsh et al.). The following is an example of how such tests are performed: A reference thromboplastin reagent of known ISI is obtained. Using this reference thromboplastin reagent and the test thromboplastin reagent, a PT determination is performed on normal and coumadin-anticoagulated plasma samples. The results are plotted as the logarithms of prothrombin times of the reference thromboplastin reagent (ordinate) vs. the test thromboplastin reagent (abscissa). Orthogonal least squares regression analysis is used to determine the slope of a straight line that best fits the data. The ISI of the test thromboplastin reagent is calculated by multiplying the ISI of the reference thromboplastin reagent by the slope of the regression line.

As noted by Kirkwood, the foregoing method for calculating the ISI of a test thromboplastin reagent represents a commonly accepted approach for determining the suitability of a thromboplastin reagent for use in the PT test. Such a test was used to demonstrate the validity and usefulness of the present invention. A recent example of the application of this method is found in an article by van den Besselaar and Bertina (1991).

Thromboplastins from cultured cells

When Quick et al. described a method for producing a thromboplastin suitable for the PT test, little was known regarding the underlying mechanisms and reactions. It is now well established that the active principle in thromboplastins and the thromboplastin reagents prepared from animal tissues such as brain, lung, and placenta is a transmembrane, lipid-associated glycoprotein known as "tissue factor" or factor III (Nemerson & Bach, 1982; Spicer et al., 1987 Nemerson, 1988). It is also widely recognized (as reviewed by Nemerson & Bach, 1982, and Drake et al., 1989) that virtually all extravascular tissues (i.e., all tissues except endothelial cells or blood cells) contain tissue factor. Furthermore, (as reviewed by Nemerson and Bach, 1982), it is known that when normal or transformed cells from extravascular tissues are grown in culture, tissue factor/thromboplastin activity also may be expressed, and that endothelial cells or white blood cells can be induced in vitro to express tissue factor by a variety of chemical or biological agents.

Attention is now directed to the prior art regarding methods for preparing thromboplastin reagents from cultured cells (as distinguished from animal tissues) and the suitability of such thromboplastin reagents for use in the PT test. A review of the recent literature disclosed the following: (1) Naito et al. (1983) prepared thromboplastins from 8 lines of cultured human gastric cancer cells by a process involving "freeze thawing and sonification" to produce a cell lysate that was subsequently extracted with "physiological saline" to yield a solution rich in thromboplastic activity. A "plasma recalcification time" was used to detect tissue factor activity, and clotting times ranging from 21.1-77.4 sec. were reported. With the exception of the cell lysis procedure, this thromboplastin was prepared according to classical methods described above; however, because the normal plasma PT was not within the range of 10-14 sec, Naito et al. (1983) does not teach a method for producing a thromboplastin reagent suitable for use in the PT test.

(2) Silverberg et al. (1989) identified tissue factor in two human pancreatic cancer cell lines and prepared solutions with thromboplastic activity from "whole cells, freeze-thawed cells, microvesicles, and membrane preparations." The preparation method was neither specified nor cross-referenced in this article. Thromboplastin activity was determined with a two-stage recalcification time test, and clotting times as low as 17 sec. were reported. Because the current PT assay procedure was not used, and because the normal plasma PT was not within the range of 10-14 sec., Silverberg et al. did not teach a method for producing a thromboplastin reagent suitable for use in the PT test.

(3) Andoh et al. (1990) taught what they described as a "one-stage method" for detecting tissue factor activity in leukemic cells. In fact, it was a two-step PT test involving (i) incubation of a leukemic cell homogenate with human plasma for 3 min. and, thereafter, (ii) addition of $CaCl_2$ to initiate coagulation. Normal plasma clotting times equal to or greater than 54 sec. were reported. Because the normal plasma PT was not within the range of 10-14 sec, Andoh et al. did not teach a method for producing a thromboplastin reagent suitable for use in the PT test.

(4) Rehemtulla et al. (1991) transfected the gene for human tissue factor into a rodent cell line, and demonstrated that the expressed recombinant human tissue factor protein exhibited physicochemical and biologic properties similar to that of its native human counterpart. A method for preparing a thromboplastin reagent was described: "Cell suspensions at $1 \times 10^6$ cells/ml in TBS [20 mM Tris, 150 mM NaCl, pH 7.4] were frozen in a dry ice/ethanol bath and thawed at 37° C. three times, and 0.1 ml of this lysate was used in a standard one-stage clotting assay to determine procoagulant activity." Without specifying the actual PT method used, the authors stated that thromboplastins produced from these freeze/thaw lysates of recombinant cells were evaluated according to two different two-step PT methods (Levy & Edgington, 1980; Tsao et al., 1984). In this example, normal plasma clotting times in the 10-14 second range indeed were obtained. However, since the assay protocols contained significant deviations from the commonly accepted procedure for the PT test it is impossible to determine whether a suitable thromboplastin reagent was produced using the freeze/thaw method. Furthermore, the raw material for the thromboplastin reagent in the example by Rehemtulla et al. was produced from recombinant rodent cells that were expressing supernormal amounts of human tissue factor. Thus, it is impossible to determine from this example of the prior art whether the thromboplastin preparation method would be appropriate for cultured non-recombinant cells, the subject of the present invention. We prepared thromboplastin reagent from cultured non-recombinant cells by the method of Rehemtulla et al. The results of this experiment, reported in Table 1, clearly indicate that this method does not yield a satisfactory reagent.

SUMMARY OF THE PRIOR ART

A useful prothrombin time test must be performed in a one-step/one stage format, with the thromboplastin reagent containing both a tissue factor-rich membranous preparation at approximately neutral pH and physiologic ionic strength and calcium at a concentration of approximately 20-30 mM. There are several methods for producing thromboplastins from animal tissues: The classical acetone extraction/dehydration procedure of Quick et al. (Biggs, 1974; p. 663), the saline extraction method (Biggs, 1974, p. 664), and a detergent extraction method (Hvatum & Prydz, 1966) that is impractical for commercial application. A distinction is made between thromboplastins produced by these methods and "thromboplastin reagents," which contain added calcium and therefore can be used in a one-step/one-stage procedure. A thromboplastin reagent prepared from human tissue is useful and preferred because such homologous thromboplastin reagents have greater sensitivity to human clotting factors than their heterologous counterparts. It is well known that cultured human cells of extravascular origin contain human tissue factor, and that thromboplastins can be produced from such cells. However, no thromboplastins produced from cultured human cells have been suitable for use in the PT test. Thus, the objective of this invention is to develop a method for producing a thromboplastin reagent suitable for use in the one-step/one-stage prothrombin time test using cultured, non-recombinant, human cells.

SUMMARY OF THE INVENTION

A method for preparing a thromboplastin reagent from cultured human cells that yields a thromboplastin reagent suitable for use in a PT test in which (i) the assay is a one-step/one-stage procedure; (ii) normal human plasma typically clots in about 10-14 seconds, with a mean normal PT of about 11-13 sec; (iii) the results are highly correlated with those from an international reference thromboplastin reagent; and (iv) the thromboplastin reagent is stable in liquid form for at least 8 hrs. at 37° C. and 5 days at 4° C.

BRIEF DESCRIPTION OF THE DRAWINGS

FIG. 1 illustrates the prothrombin times in normal plasma of a variety of test thromboplastin reagents. Three commercially available thromboplastin reagents, prepared essentially via the Quick (1938) method, are included for comparison. Thr-S: THROMBOREL®-S,thromboplastin reagent (Behringwerke AG, Marburg, Germany) was prepared from human placenta. Spl-XLS and Spl-XL: SIMPLASTIN® EXCEL-S and SIMPLASTIN® EXCEL thromboplastin reagent (Organon Teknika Corp., Durham, N.C.) were prepared from rabbit brain. The following human cell lines were evaluated: H4 (ATCC HTB 148): a human brain neuroglioma; U-87 MG (ATCC HTB 14): a grade III human glioblastoma, astrocytoma; Hs683 (ATCC HTB 138): a human glioma; WI-38 (ATCC CCL 75): from human lung; WI-38 VA13 subline 2RA (ATCC CCL 75.1): from SV40 virus-transformed human lung; SK-LU-1 (ATCC HTB 57): a human lung adenocarcinoma; Calu-1 (ATCC HTB54): an epidermoid grade III lung carcinoma; Hs888Lu (ATCC CCL 211): from human lung; JAR (ATCC HTB 144): a human placental choriocarcinoma; WISH (ATCC CCL 25): from human amnion; FHC:TAC and FHC:KEN: two in-house human histiocytomas. All except the two in-house cell lines were obtained from the ATCC, Rockville, Md.

DESCRIPTION OF THE PREFERRED EMBODIMENTS

A method for preparing a thromboplastin reagent from cultured human cells

Cell growth and harvesting. A human cell line, preferably with high constitutive expression of thromboplastin/tissue factor activity, is grown under optimized cell culture conditions to high or maximal cell density, and harvested by conventional means. Recommended cell culture conditions are provided by the ATCC, Rockville, Md. in the *ATCC Catalogue of Cell Lines and Hybridomas*, 7th Edition (1992), which are included herein by reference. Since mammalian cell lines usually require attachment to a solid substrate for maximal growth, harvesting typically will involve treatment of the culture with trypsin and/or ethylenediaminetetraacetic acid (EDTA) to suspend the cells in culture medium. However, it is also possible and not beyond the scope of the present invention that a cell line expressing sufficient tissue factor might be grown and harvested in suspension culture, thereby obviating the need for detachment of the cells from a substratum. The cells were concentrated into a pellet by centrifugation and the supernatant medium was discarded. Cells were then resuspended in a buffered isotonic salt solution (Dulbecco's phosphate-buffered saline solution; D-PBS; approximately 3-5 volume excess of D-PBS to cell pellet), and re-centrifuged to remove residual traces of culture medium, trypsin or EDTA. The cell pellet was resuspended in D-PBS and centrifuged once more, as above. The supernatant was discarded, the cell pellet was resuspended in 1-2 volume excess of D-PBS, and the mixture was frozen at $-20°$ to $-70°$ C.

Cell lysis and reconstitution in thromboplastin diluent. Frozen cells were thawed, D-PBS was added (approximately 1.5 mL per 0.1 g wet wt. of cells) and pelleted by centrifugation at approximately $10,000 \times x$ g for 30 min. The cells were resuspended in a hypotonic buffer solution containing $NaHCO_3$ (10 mM), Na-EDTA (2 mM), and bovine serum albumin (BSA; 0.5 mg/mL) to a concentration of approximately 1.5 mL buffer/0.1 g wet wt. of cells. The suspension was mixed thoroughly, and centrifuged at $10,000 \times x$ g as above. The cells were resuspended again in hypotonic buffer solution, mixed, and centrifuged at $10,000 \times x$ g, as above. Although hypotonic lysis is our preferred method, any physical means of disrupting the cells may be used.

The final cell pellet was suspended in a thromboplastin diluent containing polyethylene glycol 1450 (1.5%), NaCl (103 mM), Ca-gluconate (30 mM), $NaN_3$ (0.025%), BSA (0.25 mg/mL) and imidazole (10mM, pH 7.2) at a concentration of approximately 1 mL buffer per 0.05 g wet wt of cells.

It is contemplated within the scope of the invention to vary the approximate concentration of each component of the thromboplastin diluent as long as the reagent produces a one stage prothrombin time in about 10 to 15 seconds, with a mean normal prothrombin time of about 11 to 13 seconds, when added to citrated normal plasma in a volume ratio of about 2:1, reagent to plasma. The approximate concentration of each component may be varied by plus or minus 50%, as long as the prothrombin time remains within the range of about 10-15 seconds. In addition, Ca-gluconate can be substituted with any soluble calcium salt and NaCl can be substituted with any other salt that provides comparable ionic strength. The composition of the diluent may be varied as long as it presents an approximate physiologic ionic strength within the range of about 0.1 to 0.25 and an approximate pH range of about 6.8 to 7.8. BSA may also with substituted by other albumin, such as human serum albumin (HSA). All these variations are contemplated within the invention.

The protein concentration was determined with a BCA enhanced protein assay (Pierce Chemical Co., Rockford, IL), and the final concentration of the thromboplastin was adjusted to about 0.5 to 1-2 mg/mL.

Comparison of human cell lines for production of a thromboplastin reagent.

The general applicability of the above-described method for producing a human thromboplastin reagent has been demonstrated by preparing thromboplastin reagents from a variety of human cell lines. As is evident from FIG. 1, three commercial thromboplastin reagents exhibit prothrombin times of approximately 12-14 sec. Thromboplastin reagents prepared from six of the tested cell lines (U-87 MG, Hs683, WI-38, WI-38 VA13, Calu-1, and Hs888Lu) in accordance with the present invention exhibited normal clotting times in the range of 10-14 sec, and therefore met this criterion for a suitable human thromboplastin. This illustrates the general application and usefulness of the method. The remaining cell lines (H4, SK-LU-1, JAR, WISH, FHC:TAC and FHC:KEN) exhibited longer clotting times, presumably reflecting a lower level of tissue factor expression. These latter thromboplastin reagents are not suitable for use in the PT test.

Preparation of a thromboplastin reagent from cultured cells via the original Quick (1938) method: Lack of suitability for the prothrombin time test.

Figure 1:
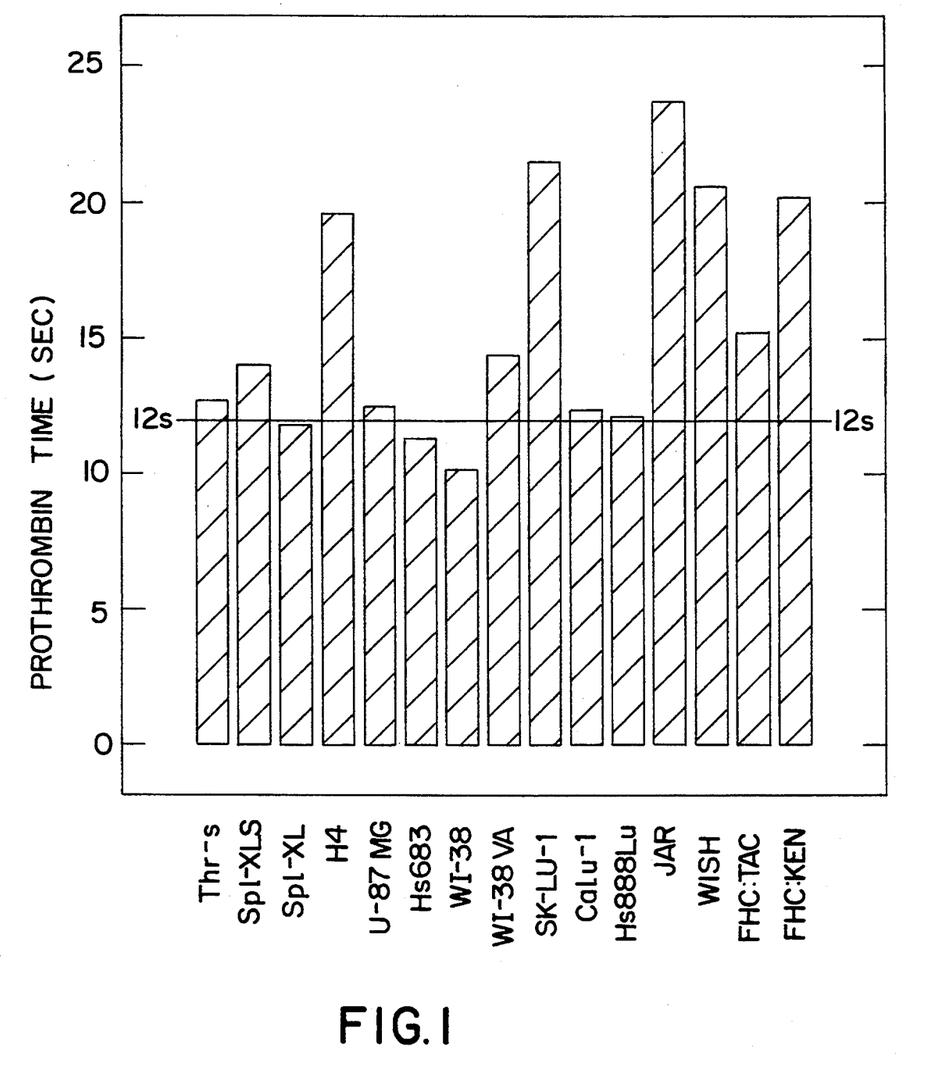

One of the cell lines described in FIG. 1, WI-38 VA13 Subline 2RA, was used as raw material to prepare a thromboplastin according to the original method of Quick (1938), involving the steps of acetone extraction, drying, and reconstitution in aqueous salt solution, as described above. This thromboplastin yielded a clotting time of 28.9 sec. in normal pooled plasma (herein defined as a human plasma preparation containing citrate-anticoagulated plasma from 20 healthy donors). As noted above, a thromboplastin suitable for use in the PT test must clot normal plasma in approximately 10-14 sec; therefore, this thromboplastin was not suitable for use in the PT test.

Figure 2:
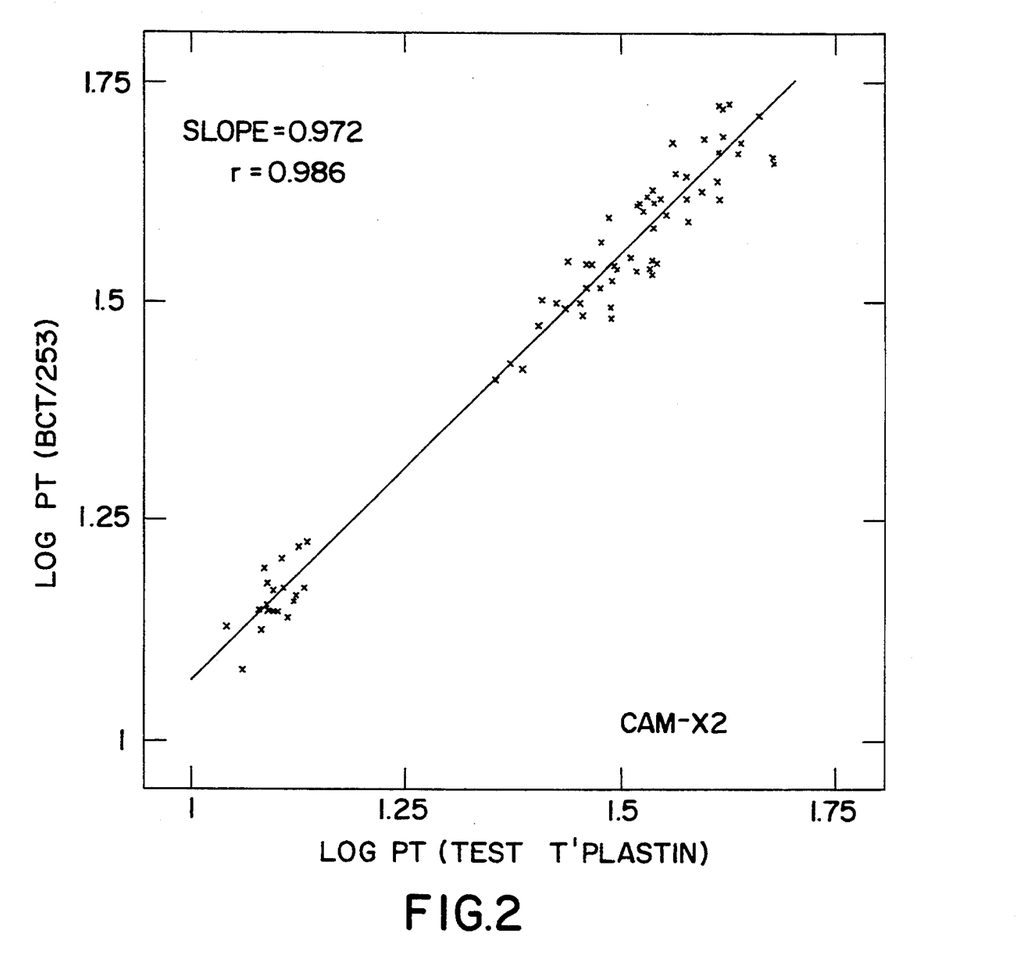
FIG. 2 illustrates a scattergram of an ISI determination performed by RELAC, an international reference laboratory based in Leiden, The Netherlands. The thromboplastin reagent from cultured cells was calibrated against an international reference standard (BCT/253), and orthogonal least squares regression analysis disclosed an ISI of 1.09 (std. dev. 0,019; N=80) with a mean normal PT of 12.6 sec. (std. dev. 0.7 sec; N=20).

Comparison of the thromboplastin from cultured cells with an international reference thromboplastin One of the cell lines described in FIG. 1, WI-38 VA13 Subline 2RA, was selected for large-scale production of a human thromboplastin reagent. This thromboplastin reagent was produced in accordance with the harvesting, cell lysis, and reconstitution procedures described above for this invention. When calibrated against a human brain international reference thromboplastin reagent (BCT/253) by RELAC, an international reference laboratory, using established and generally accepted procedures, the results presented in FIG. 2 were obtained. Summarizing from these data, which were obtained from 20 normal and 60 long-term anticoagulated plasma samples, the thromboplastin reagent produced from cultured cells exhibited a normal plasma clotting time of $12.6 \pm 0.7$ sec, and an ISI of $1.09 \pm 0.019$ (mean$\pm$std. dev.). Thus, this human thromboplastin reagent is in compliance with the above-described specifications for a thromboplastin reagent suitable for use in the PT test.

Figure 3:
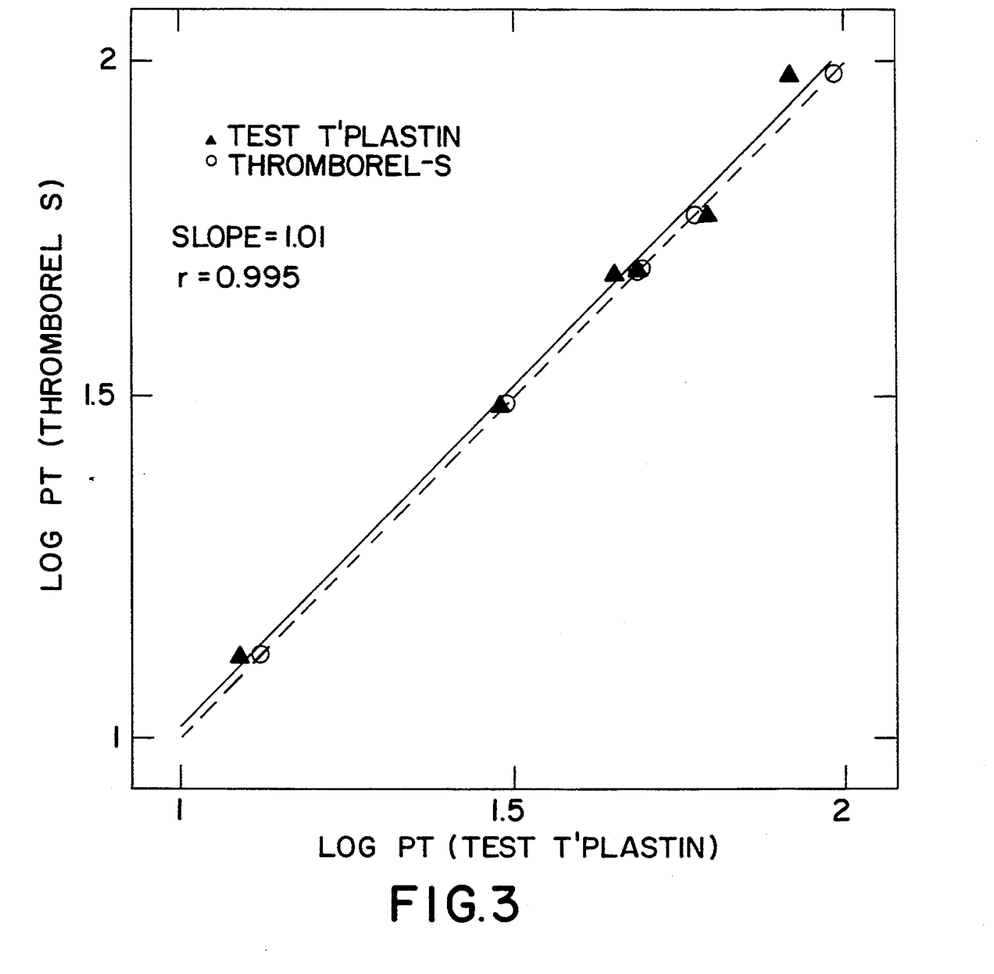
FIG. 3 illustrates a scattergram of an ISI determination performed by the inventors in which the thromboplastin reagent from cultured cells (solid line; closed triangles) was compared with a commercially available human thromboplastin reagent (THROMBOREL®-S; Behringwerke AG, Marburg, Germany) prepared from human placenta (dashed line; open circles). The results were highly correlated (r=0.995), and thereby demonstrate the suitability of the thromboplastin reagent from cultured cells for use in a PT test.

Comparison of the thromboplastin reagent from cultured cells with a commercially available human thromboplastin reagent The ISI determination procedure was used to compare the thromboplastin reagent prepared from cultured cells according to the invention with a commercially available human thromboplastin reagent (Thromborel®-S; Behringwerke AG, Marburg, Germany) prepared from human placenta. In this example, the plasma samples consisted of fresh-frozen normal plasma, two lyophilized abnormal plasma preparations (Verify Abnormal I; Verify Abnormal II; Organon Teknika Corp., Durham, N.C.) and three plasma samples from patients receiving long-term oral anticoagulation. The results (FIG. 3) were highly correlated (r=0.995), thereby again demonstrating the suitability of the thromboplastin reagent from cultured cells for use in a PT test.

Comparison of a thromboplastin reagent prepared according to the method of the present invention with thromboplastin reagents prepared according to the acetone extraction/dehydration or saline extraction methods described in Biggs (1976) pp. 663–664 and the freeze-thaw cell lysis method of Rehemtulla et al. (1991)

The above-referenced methods involving acetone or saline extraction of tissue or freeze-thaw lysis of cultured cells represent approaches to producing thromboplastins extant in the prior art. A thromboplastin reagent was prepared from cultured, non-recombinant, human lung cells using each of these three methods. In accordance with accepted procedures (Biggs, 1976; p. 677) each thromboplastin was made 25 mM in calcium chloride to yield a thromboplastin reagent as defined above. The PT test results for thromboplastin reagents prepared according to the three prior-art methods were compared with those of a thromboplastin reagent prepared according to the method of the present invention.

Figure 4:
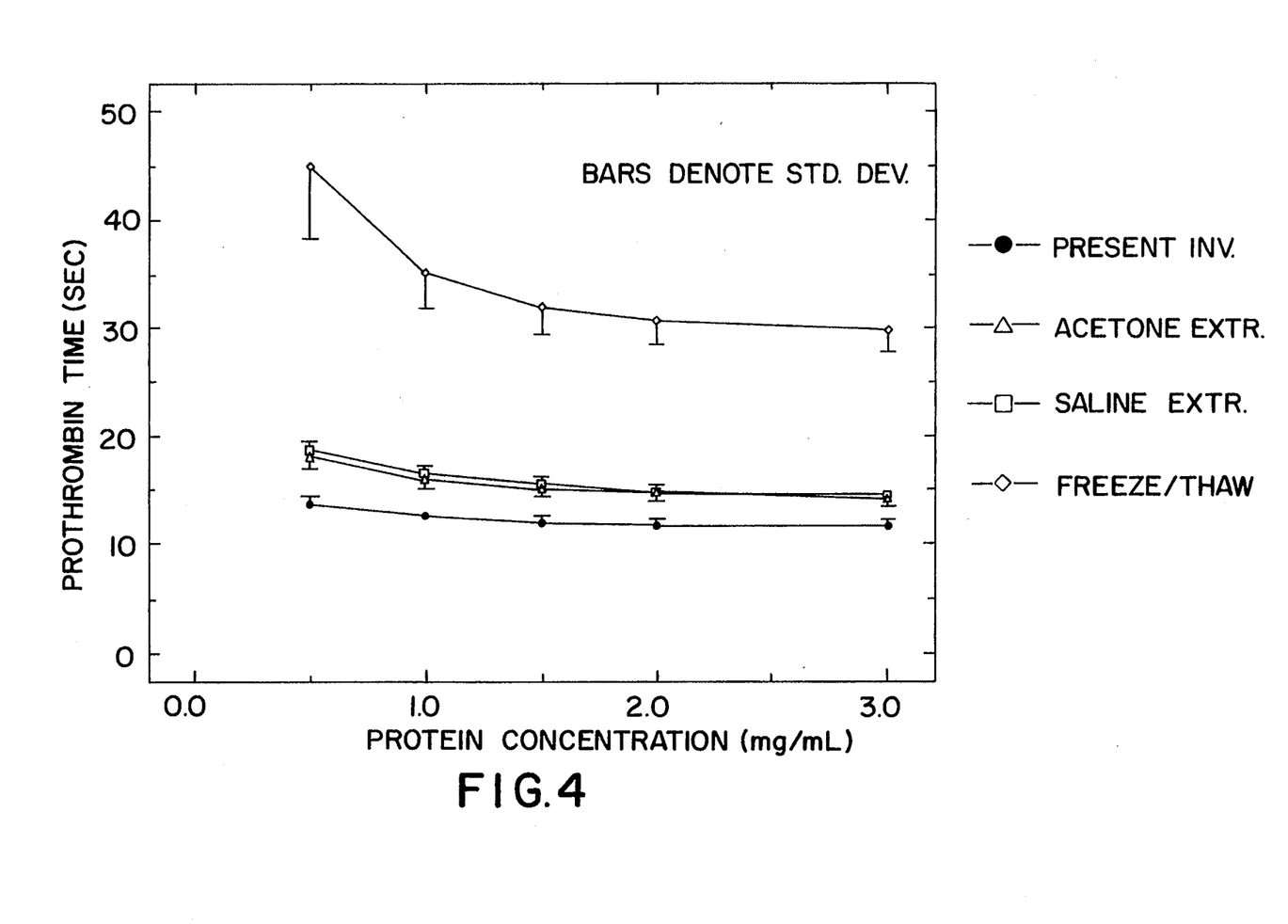
FIG. 4 illustrates the mean PT obtained for a panel of 6 normal plasma samples (each determined in duplicate) versus the thromboplastin protein concentration (determined with the BCA enhanced protein assay, vide infra). Error bars denote standard deviations from the mean PT of 6 samples.

Each of the four thromboplastin reagents was evaluated at protein concentrations (determined by the above-referenced method) ranging from 0.5 to 3.0 mg/mL. The prothrombin time at each protein concentration is shown in Table 1 and FIG. 4. The results indicate that thromboplastin reagents prepared via methods disclosed in the prior art would not be suitable for use in the PT test because the normal plasma PT results are above the acceptable range of 10–14 sec.

TABLE 1

Comparison of Thromboplastin reagents Pepared by Different Methods Prothrombin Times for Normal Pooled Plasma

| THROMBO-PLASTIN PROTEIN CONC. (mg/mL) | CLOTTING TIME (sec) | | | |
|---|---|---|---|---|
| | Present Invention | Freeze-thawing[1] | Acetone Extraction[2] | Saline Extraction[3] |
| 0.5 | 12.9 | 26.9 | 18.8 | 17.9 |
| 1.0 | 12.2 | 24.5 | 18.0 | 18.1 |
| 1.5 | 11.5 | 23.3 | 17.5 | 16.9 |
| 2.0 | 11.2 | 22.7 | 16.3 | 16.6 |
| 3.0 | 10.9 | 21.0 | 15.4 | 15.3 |

[1]Rehemtulla et al. (1991)
[2]Biggs et al. (1976; p. 663)
[3]Biggs et al. (1976; p. 664)

It will be noted from Table 1 that within the range of protein concentration assayed, all of the prothrombin times for the thromboplastin reagent prepared according to the method of the present invention are below 13 sec, and therefore this thromboplastin reagent is suitable for use in the prothrombin time test. However, none of the prothrombin times for thromboplastin reagents prepared from the same cultured human lung cells according to methods disclosed in the prior art were less than 14 sec. Thus, these thromboplastin reagents would not be suitable for use in the PT test. The conclusion from this experiment is that the prior art does not disclose a feasible method for producing a thromboplastin reagent from cultured human cells that also is suitable for use in the PT test.

This conclusion is supported by the results from a second experiment in which the four thromboplastin reagents described above were evaluated in the PT test against a panel of 6 normal plasma samples. In this experiment the mean normal PT was obtained for each thromboplastin reagent at each of the 5 protein concentrations. As noted above, the mean normal PT of a useful thromboplastin reagent will be about 11–13 sec. The mean normal PT of the thromboplastin reagent prepared according to the method of the present invention was compared with the corresponding values for the 3 thromboplastin reagents prepared according to the three prior art methods described above. The results (FIG. 4) disclosed that (i) at each protein concentration the thromboplastin reagent prepared according to the method of the present invention exhibited a significantly lower PT (p<0.001; Student's t test) than the counterparts prepared via the other methods; and (ii) the mean normal PT for the thromboplastin reagent prepared according to the method of the present invention ranged from 11.6–13.7 sec, whereas that for the other three thromboplastin reagents ranged from 14.3 sec. at the highest protein concentration (3 mg/mL) to 45 sec. at the lowest protein concentration (0.5 mg/mL). It is not impossible that a thromboplastin reagent prepared according to prior-art methods and formulated at protein concentrations (BCA protein determination method) exceeding about 3 mg/mL might be suitable for use in the PT test; however, such a formulation would be beyond the scope and claims of the present invention. Summarizing, this experiment illustrates that, in the thromboplastin concentration range of 0.5 to 3.0 mg/mL, a thromboplastin reagent formulated according to the method of the present invention exhibits significantly (p<0,001) shorter prothrombin times than thromboplastin reagents formulated according to methods disclosed in the prior art. This shorter prothrombin time enables the invention of a new and useful thromboplastin reagent from cultured cells.

Stability of the thromboplastin reagent from cultured cells

When formulated as described above, the thromboplastin reagent from cultured human cells is stable for 1–3 days at 37° C., and for at least 3 months in liquid form at 4° C. Stability was assessed by measuring the clotting times of normal and abnormal plasma samples over the indicated intervals. The stability of this thromboplastin reagent under these conditions supports the conclusion that it is suitable for use in the PT test.

References

Andoh, K., Sadakata, H., Uchiyama, T., Narahara, N., Tanaka, H., Kobayashi, N., and Maekawa, T. (1990) One-stage method for assay of tissue factor activity of leukemic cell with special reference to disseminated intravascular coagulation. *Amer. J. Clin. Pathol.* 93:679–684

Biggs, R. (1976) "Human Blood Coagulation, Haemostasis and Thrombosis." 2nd edition. Blackwell Scientific Publications, London.

Drake, T. A., Morrissey, J. H., and Edgington, T. S. (1989) Selective cellular expression of tissue factor in human tissues. *Am. J. of Pathol.* 134:1087–1097

Hirsch, J., Poller, L., Deykin, D., Levine, M., and Dalen, J. E. (1989) Optimal therapeutic range for oral anticoagulants. *Chest* 95:5S-11S Hvatum, M., Prydz, H. (1966) Studies on tissue thromboplastin. I. Solubilization with sodium deoxycholate. *Biochim. Biophys. Acta* 130:92–101

Kirkwood, T. B. L. (1983) Calibration of reference thromboplastins and standardisation of the prothrombin time ratio. *Thromb. Hemostas.* 49:238–244

Levy, G. A. and Edgington, T. S. (1980) Lymphocyte cooperation is required for amplification of macrophage procoagulant activity. *J. Exp. Med.* 151:1232–1244

Naito, S., Inoue, S., Kinjo, M., and Tanaka, K. (1983) Thromboplastic and fibrinolytic activities of cultured human gastric cancer cell lines. *Gann* 74:240–247

Nemerson, Y. (1988) Tissue factor and hemostasis. *Blood* 71:1–8

Nemerson, Y., Bach, R. (1982) Tissue factor revisited. *Hemostas. Thromb.* 6:237–261

Quick, A. J., Stanley-Brown, M., Bancroft, F. W. (1935) A study of the coagulation defect in hemophilia and in jaundice. *Am. J. Med. Sci.* 190:501–511

Quick, A. J, (1938) The nature of bleeding in jaundice. *J. Am. Med. Assoc.* 110:1658–1662

Rapaport, S. I. (1991) Regulation of the tissue factor pathway. *Ann. NY Acad. Sci.* 614:63–75

Rehemtulla, A., Pepe, M., Edgington, T. S. (1991) High level expression of recombinant human tissue factor in Chinese hamster ovary cells as a human thromboplastin. *Thromb. Haemostas.* 65:521–527

Silverberg, J. M., Gordon, S., and Zucker, S. (1989) Identification of tissue factor in two human pancreatic cancer cell lines. *Cancer Res.* 49:5443–5447

Spicer, E. K., Horton, R., Bloem, L., Bach, R., Williams, K. R., Guha, A., Kraus, J., Lin, T-C, Nemerson, Y., and Konigsberg, W. H. (1987) Isolation of cDNA clones coding for human tissue factor: Primary structure of the protein and CDNA. *Proc. Natl. Acad. Sci., USA* 84:5148–5152

Tsao, B. P., Fair, D. S., Curtiss, L. K., and Edgington, T. S. (1984) Monocytes can be induced by lipopolysaccharide-triggered T lymphocytes to express functional factor VII/VIIa protease activity. *J. Exp. Med.* 159:1042–1057 van den Besselaar, A. M. H. P. and Bertina, R. M. (1991) Multi-center calibration of the second reference material for thromboplastin, rabbit, plain, coded CRM 149R. *Thromb. Haemostas.* 65:263–267

We claim:

1. A method for preparing a human thromboplastin reagent from cultured non-recombinant human cells comprising the steps of washing the cultured human cells with an isotonic aqueous salt solution, said cells produce an amount of tissue factor sufficient to produce a one-stage prothrombin time in plasma of about 10 to about 15 seconds, lysing the cells, isolating membranous material from the lysed cells as a pellet and resuspending the isolated membranous material in an aqueous diluent having approximately physiologic ionic strength within the range of about 0.1 to 0.25, said diluent comprises polyethylene glycol in an amount of from about 0,5 to 2.5% by weight, NaCl at a concentration of about 50 to 150 mM, Ca-gluconate at a concentration of about 10 to 5 mM, $NaN_3$ in a concentration of about 0.01 to about 0.1% by weight, bovine serum albumin at a concentration of about 0.1 to 10 mg/mL, and imidazole at a concentration of about 5 to 75 mM, and wherein the diluent has a pH range of about 6.8 to 7.8, whereby a thromboplastin reagent capable of producing a one-stage prothrombin time in plasma of about 10 to about 15 seconds is obtained.

2. The method of claim 1, wherein the cells are lysed by hypotonic shock.

3. The method of claim 1 wherein the cultured non-recombinant human cells are selected from the group consisting of, Hs683 (ATCC HTB 138), WI-38 (ATCC CCL 75), WI-38 VA13 subline 2RA (ATCC CCL 75.1), and Hs888Lu (ATCC CCL 211).

4. The method of claim 2 wherein the cultured non-recombinant human cells are selected from the group consisting of, Hs683 (ATCC HTB 138), WI-38 (ATCC CCL 75), WI-38 VA13 subline 2RA (ATCC CCL 75.1), and Hs888Lu (ATCC CCL 211).

5. The method of claim 1 wherein said cells are physically lysed.

6. The method of claim 2 wherein said cells are lysed by hypotonic shock in a buffered solution containing EDTA and albumin.

7. The method of claim 1 wherein the diluent comprises 1.5% polyethylene glycol, 103 mM NaCl, 30 mM Ca-gluconate, 0.025 $NaN_3$, 0.25 mg/mL bovine serum albumin and 10 mM imidazole.

8. The method of claim 5 wherein said cells are lysed in a buffered solution containing EDTA and albumin.

9. The method of claim 5 wherein the cultured non-recombinant human cells are selected from the group consisting of, Hs683 (ATCC HTB 138), WI-38 (ATCC CCL 75), WI-38 VA13 subline 2RA (ATCC CCL 75.1), and Hs888Lu (ATCC CCL 211).

* * * * *